United States Patent [19]

Belani

[11] Patent Number: 5,905,155

[45] Date of Patent: May 18, 1999

[54] PROCESS FOR THE PREPARATION OF AN OPTICALLY PURE TETRAHYDROQUINOLINE CARBOXYLIC ACID

[75] Inventor: Piero Belani, Rho, Italy

[73] Assignee: Archimica SPA, Origgio, Italy

[21] Appl. No.: 08/898,949

[22] Filed: Jul. 23, 1997

[30] Foreign Application Priority Data

Jul. 29, 1996 [IT] Italy ................................. MI96A1607

[51] Int. Cl.⁶ .................................................. C07D 217/16
[52] U.S. Cl. ............................................................ 546/147
[58] Field of Search ............................................. 546/147

[56] References Cited

U.S. PATENT DOCUMENTS

| | | | |
|---|---|---|---|
| 5,602,255 | 2/1997 | Kuge | 546/147 |
| 5,610,307 | 3/1997 | Erickson | 546/147 |
| 5,627,282 | 5/1997 | Kwon et al. | 546/147 |

FOREIGN PATENT DOCUMENTS

| | | |
|---|---|---|
| 0 533 000 | 3/1993 | European Pat. Off. . |
| 0 578 163 | 1/1994 | European Pat. Off. . |
| 0 636 612 | 2/1995 | European Pat. Off. . |
| 97 17050 | 5/1997 | WIPO . |

OTHER PUBLICATIONS

Fiesers' Reagents for Organic Synthesis, vol. 9, p. 238, 1981.

Primary Examiner—Alan L. Rotman
Assistant Examiner—D. Margaret M. Mach
Attorney, Agent, or Firm—Michael N. Meller

[57] ABSTRACT

A process for the preparation of optically pure (−)-1,2,3,4-tetrahydroquinoline-3-carboxylic acid by reaction of L-phenylalanine with formaldehyde in aqueous solution or paraformaldehyde in the presence of hydroiodic acid is described.

22 Claims, No Drawings

PROCESS FOR THE PREPARATION OF AN OPTICALLY PURE TETRAHYDROQUINOLINE CARBOXYLIC ACID

The present invention relates to a process for the preparation of optically pure (−)-1,2,3,4-tetrahydroquinoline-3-carboxylic acid of formula A

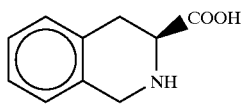
(A)

This product is the key intermediate in the preparation of pharmaceutically active compounds, especially of psychotropic and anti-retroviral agents.

The most efficient known process for the preparation of the above acid is described in EP 636.612. According to that process, L-phenylalanine is reacted with hydrobromic acid and formaldehyde to obtain the desired product with a yield of 85.4% and an optical purity of 97%.

That same document describes the preparation of (−)-6-hydroxy-1,2,3,4-tetrahydroquinoline-3-carboxylic acid with an optical purity of 100% and a yield of 95%, from m-tyrosine in accordance with the same method. However, where L-phenylalanine is used as the starting material, it is not possible to obtain a (−)-1,2,3,4-tetrahydroquinoline-3-carboxylic acid with 100% optical purity.

It has now been found that this result is achieved if the reaction between formaldehyde and L-phenylalanine is carried out in the presence of hydroiodic acid.

It has also been found that the reaction can be readily standardised and transferred to pilot and industrial plants, without the optical purity of the resulting product being reduced, with yields of never less than 95–96%.

Thus, the present invention relates to a process for the preparation of optically pure (−)-1,2,3,4-tetrahydroquinoline-3-carboxylic acid, characterised in that the L-phenylalanine is treated with formaldehyde in the presence of hydroiodic acid. The formaldehyde can be used in the form of its aqueous solution (formalin) or, preferably, in the form of paraformaldehyde.

The hydroiodic acid is used in aqueous solution, advantageously a 50–60% aqueous solution, preferably a 55% aqueous solution. The molar ratios of L-phenylalanine to formaldehyde are from 1.1 to 1.7, preferably from 1.4 to 1.5.

The reaction between L-phenylalanine and formaldehyde, especially paraformaldehyde, in the presence of hydroiodic acid is advantageously carried out at a temperature of from 60 to 80° C., preferably from 65 to 75° C. At that temperature, the reaction is complete after from 3 to 4 hours of heating.

The (−)-tetrahydroquinoline-3-carboxylic acid so obtained is isolated by rendering the reaction mixture alkaline and precipitating the free acid by neutralisation with a strong acid, preferably with hydrochloric acid.

According to a preferred method, the isolation is carried out by adjusting the pH of the reaction mixture to from 12.0 to 12.5, then adding an alkaline thiosulphate, and finally neutralising, adjusting the pH to from 5.0 to 5.5.

The adjustment of the pH to a value of from 12.0 to 12.5 is advantageously carried out with an aqueous sodium hydroxide solution. Sodium thiosulphate is preferably used as the alkaline thiosulphate.

The neutralisation is effected by adjusting the pH of the solution to from 5.0 to 5.5, preferably with hydrochloric acid in aqueous solution.

The (−)-1,2,3,4-tetrahydroquinoline-3-carboxylic acid precipitates from the above solution and is separated by filtration, washed and dried.

The product is thus obtained with a yield of at least 95% and with an optical purity of 100% or at any rate with an amount of (+) isomer not detectable by HPLC with the use of chiral phase columns.

The reaction was monitored by HPLC under the following conditions:
 column: Lichrosorb RP-8, 7μ, 250×4 mm;
 mobile phase: A) 0.1% peracetic acid B) acetonitrile;
 gradient: at 6 minutes: 100% A; in 30 minutes changes to 50% A;
 flow: 1.5 ml/min;
 detector: UV 215 nm.

The optical purity of the isolated product is 100% and is verified by HPLC under the following conditions:
 column: Sumichiral OA-5000, 5μ, 150×4.6 mm (temperature: 35° C.);
 mobile phase: copper sulphate 0.002 M/acetonitrile (85:15);
 flow: 1.2 ml/min.;
 detector: UV 250 nm.

The following Example illustrates the invention without limiting it, however.

EXAMPLE

A mixture of 140 ml of 55% hydroiodic acid, 68 g of L-phenylalanine and 18 g of paraformaldehyde is placed under a nitrogen atmosphere, with agitation, and heated at 70° C. for 3 hours 30 minutes, the progress of the reaction being monitored by HPLC. When the reaction is complete, 300 ml of water are added to the cooled reaction mixture and subsequently, at a temperature of from 15 to 25° C., approximately 150 ml of sodium hydroxide are added dropwise in order to adjust the pH of the mixture to approximately 12.3 and to obtain a clear solution to which 3 g of sodium thiosulphate are added, agitation being effected until complete dissolution has been obtained.

Approximately 40 ml of hydrochloric acid are added dropwise at from 15 to 25° C. to the solution so obtained in order to adjust the pH to a value of not less than 5.0, thus completing the precipitation of the end product which is filtered, washed in succession with 600 ml of water and 150 ml of acetone and dried under a vacuum at 70° C. for from 15 to 20 hours. 70 g (yield: 96%) of (−)-1,2,3,4-tetrahydroquinoline-3-carboxylic acid having an optical purity of 100% are thus obtained.

$[\alpha]_D = -139°$ (c=1, HCl N).

$^1$H-NMR (200 MHz, DMSO-$d_6$+TFAd, p.p.m.):3.15 (1H, dd,J=11.3 and 17.2 Hz); 3.35 (1H,dd,J=5.3 and 17.2 Hz); 4.39 (2H,s,N—CH$_2$); 4.47 (1H,dd,J=5.3 and 11.3 Hz, N—CH); 7.28 (4H,s,arom.).

I claim:
1. A process for the preparation of optically pure (−)-1,2,3,4-tetrahydroquinoline-3-carboxylic acid for formula A

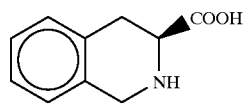
(A)

which comprises
 reacting L-phenylalanine with formaldehyde in the presence of hydroidic acid.

2. Process according to claim 1, wherein the formaldehyde is in the form of paraformaldehyde.

3. Process according to claim 2, wherein the hydroiodic acid is used as a 50–60% aqueous solution.

4. Process according to claim 3, wherein the aqueous solution of hydroiodic acid is 55%.

5. Process according to claims 2, wherein the reaction between L-phenylalanine and formaldehyde is carried out in the presence of hydroiodic acid at a temperature of from 60 to 80° C.

6. Process according to claim 3, wherein the reaction between L-phenylalanine to formaldehyde is carried out in the presence of hydroidic acid at a temperature of from 60 to 80° C.

7. Process according to claim 4, wherein the reaction between L-phenylalanine and formaldehyde is carried out in the presence of hydroiodic acid at a temperature of from 60 to 80° C.

8. Process according to claim 2, wherein the end product is isolated by adjusting the pH of the reaction mixture to from 12.0 to 12.5, adding an alkaline thiosulphate and neutralizing to a pH of from 5.0 to 5.5.

9. Process according to claims 3, wherein the end product is isolated by adjusting the pH of the reaction mixture to from 12.0 to 12.5, adding an alkaline thiosulphate and neutralizing to a pH of from 5.0 to 5.5.

10. Process according to claim 4, wherein the end product is isolated by adjusting the pH of the reaction mixture to from 12.0 to 12.5, adding an alkaline thiosulphate and neutralizing to a pH of from 5.0 to 5.5.

11. Process according to claim 1, wherein the reaction between L-phenylalanine and formaldehyde is carried out in the presence of hydroiodic acid at a temperature of from 60 to 80° C.

12. Process according to claim 11, wherein the molar ratios of L-phenylalanine to formaldehyde are from 1.1 to 1.7.

13. Process according to claim 12, wherein the mole ratio is from 1.4 to 1.5.

14. Process according to claim 11, wherein the operation is carried out at from 65 to 75° C. for from 3 to 4 hours.

15. Process according to claim 11, wherein the end product is isolated by adjusting the pH of the reaction mixture to from 12.0 to 12.5, adding an alkaline thiosulphate and neutralizing to a pH of from 5.0 to 5.5.

16. Process according to claim 12, wherein the end product is isolated by adjusting the pH of the reaction mixture to from 12.0 to 12.5, adding an alkaline thiosulphate and neutralizing to a pH of from 5.0 to 5.5.

17. Process according to claim 13, wherein the end product is isolated by adjusting the pH of the reaction mixture to from 12.0 to 12.5, adding an alkaline thiosulphate and neutralizing to a pH of from 5.0 to 5.5.

18. Process according to claim 14, wherein the end product is isolated by adjusting the pH of the reaction mixture to from 12.0 to 12.5, adding an alkaline thiosulphate and neutralizing to a pH of from 5.0 to 5.5.

19. Process according to claim 1, wherein the end product is isolated by adjusting the pH of the reaction mixture to from 12.0 to 12.5, adding an alkaline thiosulphate and neutralizing to a pH of from 5.0 to 5.5.

20. Process according to claim 19, wherein the pH of the reaction mixture is adjusted to from 12.0 to 12.5 by a sodium hydroxide solution.

21. Process according to claim 19, wherein sodium thiosulphate is used as the alkaline thiosulphate.

22. Process according to claim 19, wherein the neutralization is carried out using hydrochloric acid.

\* \* \* \* \*